United States Patent
Buckles et al.

[19]

[11] Patent Number: 6,062,902
[45] Date of Patent: May 16, 2000

[54] CONNECTOR FOR CATHETER ELECTRODE

[75] Inventors: David S. Buckles, Palm Beach Gardens; Robert E. Henderson, Port St. Lucie, both of Fla.

[73] Assignee: GE Marquette Medical Systems, Milwaukee, Wis.

[21] Appl. No.: 09/161,641

[22] Filed: Sep. 28, 1998

[51] Int. Cl.[7] .................................................. H01R 11/00
[52] U.S. Cl. .......................................... 439/502; 607/122
[58] Field of Search ..................................... 439/502, 189, 439/278, 505, 623, 909; 600/372, 373, 376, 508, 395, 483

[56] References Cited

U.S. PATENT DOCUMENTS

| | | | |
|---|---|---|---|
| 4,362,166 | 12/1982 | Furler et al. | 128/670 |
| 4,498,719 | 2/1985 | Juris et al. | |
| 4,632,121 | 12/1986 | Johnson et al. | 128/639 |
| 4,768,970 | 9/1988 | Nestor | 439/278 |
| 5,358,422 | 10/1994 | Schaffer et al. | 439/346 |
| 5,509,822 | 4/1996 | Negus et al. | 439/502 |
| 5,545,193 | 8/1996 | Fleischman et al. | 607/99 |
| 5,573,412 | 11/1996 | Anthony | 439/133 |
| 5,573,424 | 11/1996 | Poppe | 439/502 |
| 5,603,623 | 2/1997 | Nishikawa et al. | 439/144 |
| 5,660,555 | 8/1997 | Ito et al. | 439/278 |
| 5,733,323 | 3/1998 | Buck et al. | 607/122 |

*Primary Examiner*—Lincoln Donovan
*Assistant Examiner*—Michael C. Zarroli
*Attorney, Agent, or Firm*—Michael Best & Friedrich; Christian G. Cabou; Phyllis Y. Price

[57] ABSTRACT

A connector assembly for use in connecting an intracardiac catheter having a bare end connector to a patient monitor. The assembly includes an adapter, a terminal block and a cable. The adapter has an elongate insulating conductive member defined by an intermediate portion and opposite ends. A first connector is electrically connected to and is mounted at one end of the conductive member and a second connector is disposed at the other end of the conductive member. The first connector includes a first terminal connected to the conductive member for electrically engaging a bare pin connector in a surrounding relation and a tubular insulating cover extending from the one end of the adapter for telescopingly receiving the first terminal and the bare pin connector. The second connector includes a second terminal connected to the conductive member and extending from the other end of the conductive member and an insulating skirt mounted on the second connector in surrounding relation to the second terminal. The terminal block has a plurality of sockets, each socket comprising a recess complementary to the insulating skirt for receiving and securing the skirt therein, and a plurality of third terminals one of which is disposed in each socket and each being electrically engageable with the second terminal. The cable has a plurality of individual conductors each connected at one end respectively to one of said third terminals and a plug at its other end for connection to a patient monitor.

6 Claims, 4 Drawing Sheets

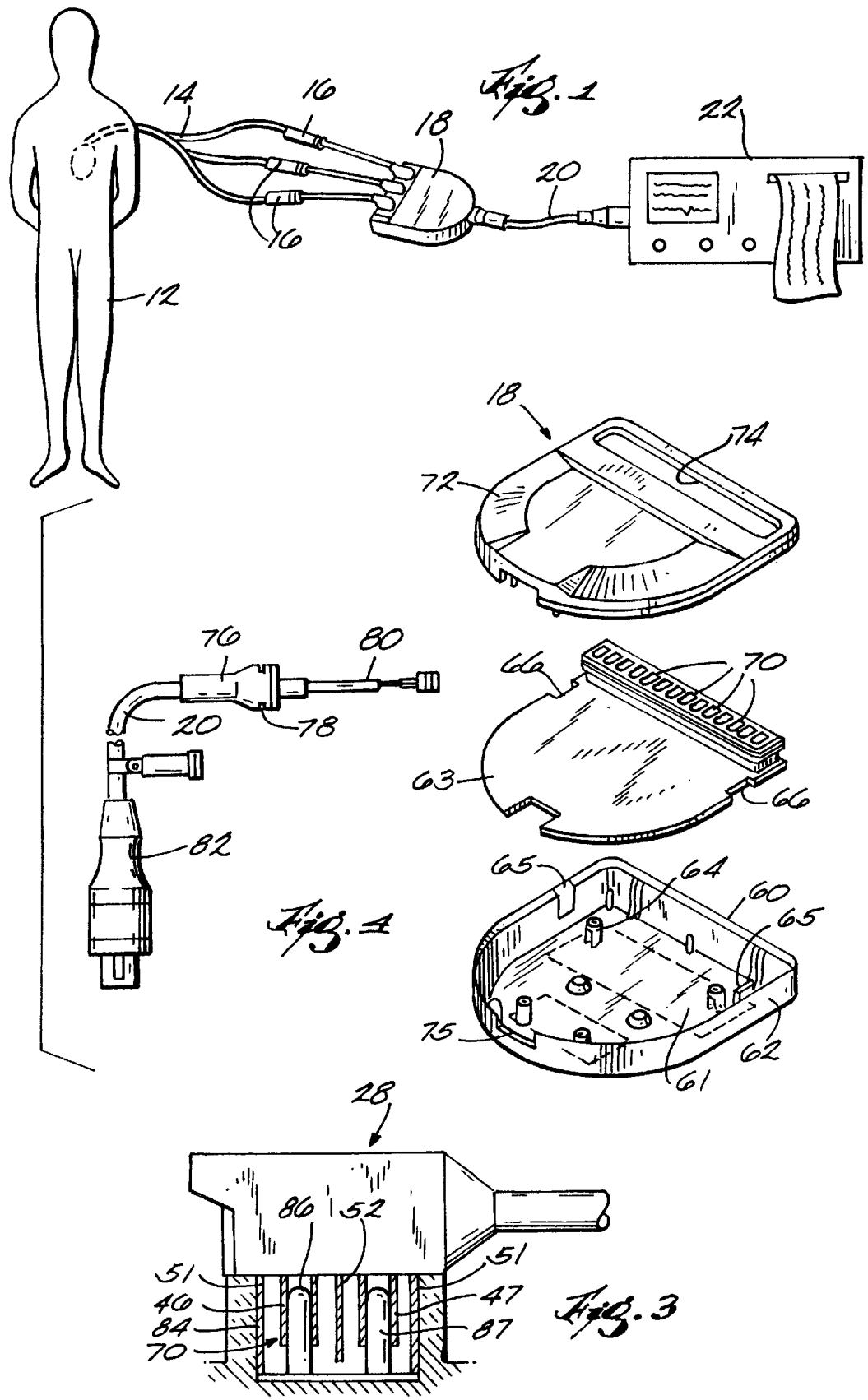

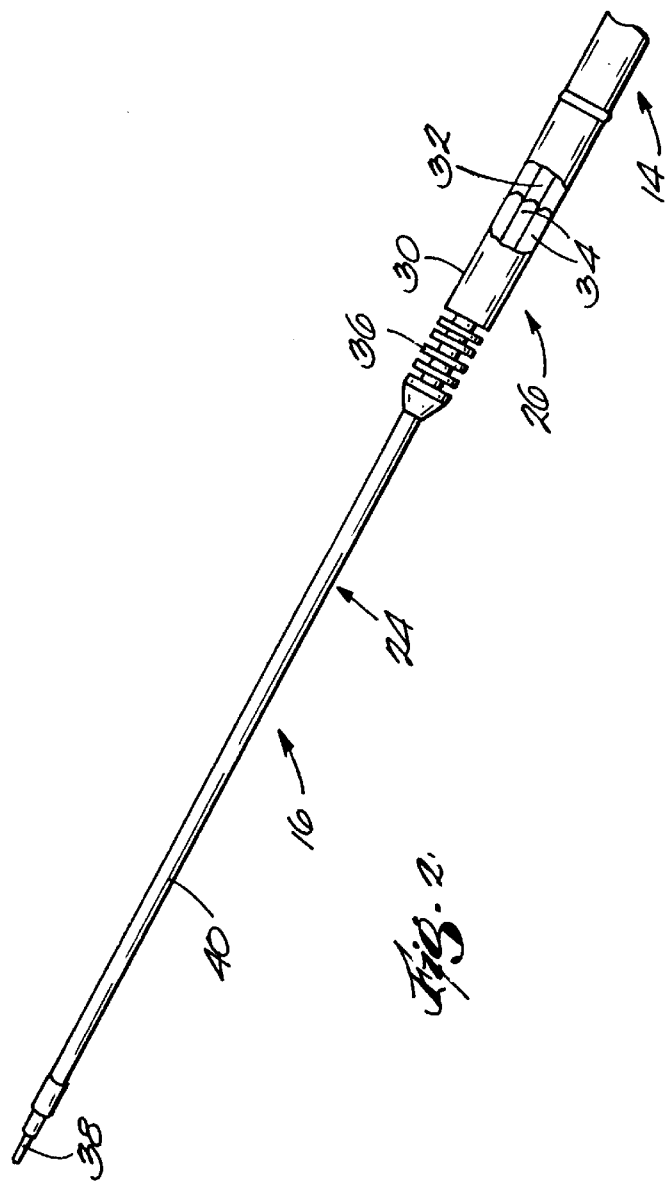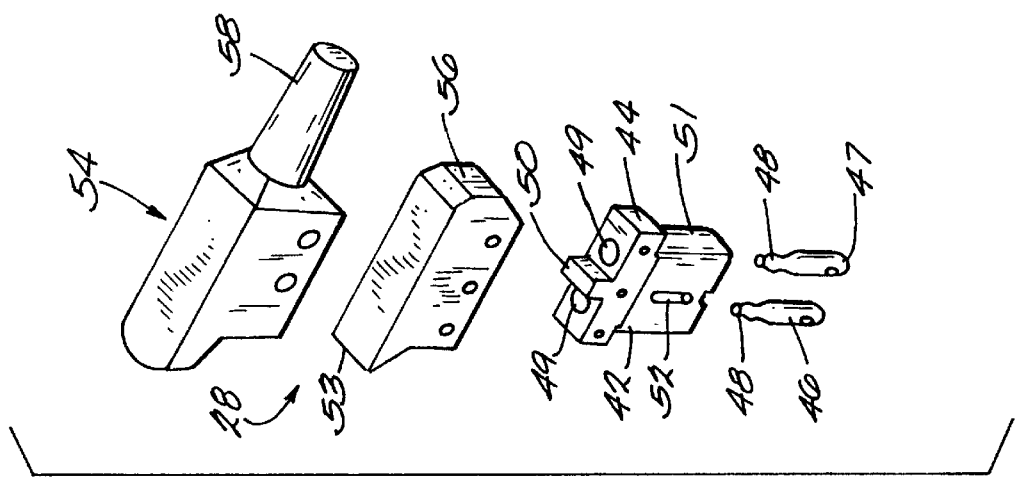

CONNECTOR FOR CATHETER ELECTRODE

BACKGROUND OF THE INVENTION

This invention relates to electrical connectors and more particularly to an electrical connector for connecting a catheter to a monitoring or recording device.

Catheters are commonly employed for a variety of medical purposes, such as monitoring various physiological functions, stimulating or ablating tissue, sampling bodily fluids and the like. Such catheters commonly comprise an elongate flexible plastic member adapted to be positioned in a body cavity. When used for monitoring physiological functions, such as intracardiac electrocardiograms or for stimulating or ablating tissue, such catheters normally include one or more sensors and/or electrodes adjacent to its distal end. Electrical conductors extend through lumens formed in the catheter between the electrodes and/or sensors to terminals at the proximal end of the catheter.

Prior art intracardiac electrode catheters included bare metal pin connectors at their proximal end for connection to monitoring or recording devices. Such bare metal electrodes were not wholly satisfactory because of susceptibility to contacting electrical grounds or sources of electrical energy.

SUMMARY OF THE INVENTION

It is an object of the invention to provide a connector for intracardiac electrode catheters which prevents accidental contact between electrode pins and electrical grounds or sources of electrical energy.

A further object of the invention is to provide a physically stable and secure connection between intracardiac catheters and monitoring or recording devices.

A still further object of the invention is to provide a means for connecting an intracardiac catheter and a monitoring device which also permits rapid connection of the catheter to stimulating devices.

These and other objects and advantages of the invention will become more apparent from the detailed description thereof taken with the accompanying drawings.

In general terms, the invention comprises a connector assembly for use in connecting an intracardiac catheter having a bare end connector to a patient monitor. The assembly includes an adapter having an elongate insulating conductive member defined by an intermediate portion and opposite ends. A first connector is electrically connected to and is mounted at one end of the conductive member and a second connector is disposed at the other end of the conductive member. The first connector includes a first terminal connected to the conductive member for electrically engaging a bare pin connector in a surrounding relation and a tubular insulating cover extending from the one end of the adapter for telescopingly receiving the first terminal and the bare pin connector. The second connector includes a second terminal connected to the conductive member and extending from the other end of the conductive member and an insulating skirt is mounted on the second connector in surrounding relation to the second terminal. The assembly includes a terminal block having a plurality of sockets, each socket comprising a recess complementary to the insulating skirt for receiving and securing the skirt therein, and a plurality of third terminals one of which is disposed in each socket and each being electrically engageable with the second terminal. A cable has a plurality of individual conductors each connected at one end respectively to one of said third terminals a plug at its other end for connection to a patient monitor.

BRIEF DESCRIPTION OF THE DRAWINGS

FIG. 1 illustrates a connector assembly according to the invention for connecting an intracardiac catheter to a monitoring device;

FIG. 2 is an exploded view of the connector which forms a portion of the invention;

FIG. 3 is an enlarged fragmentary view, partly in sections, of the connector illustrated in FIG. 2;

FIG. 4 is an exploded view of the connector block which forms a portion of the invention;

DETAILED DESCRIPTION OF THE PREFERRED EMBODIMENT

Figure 5:
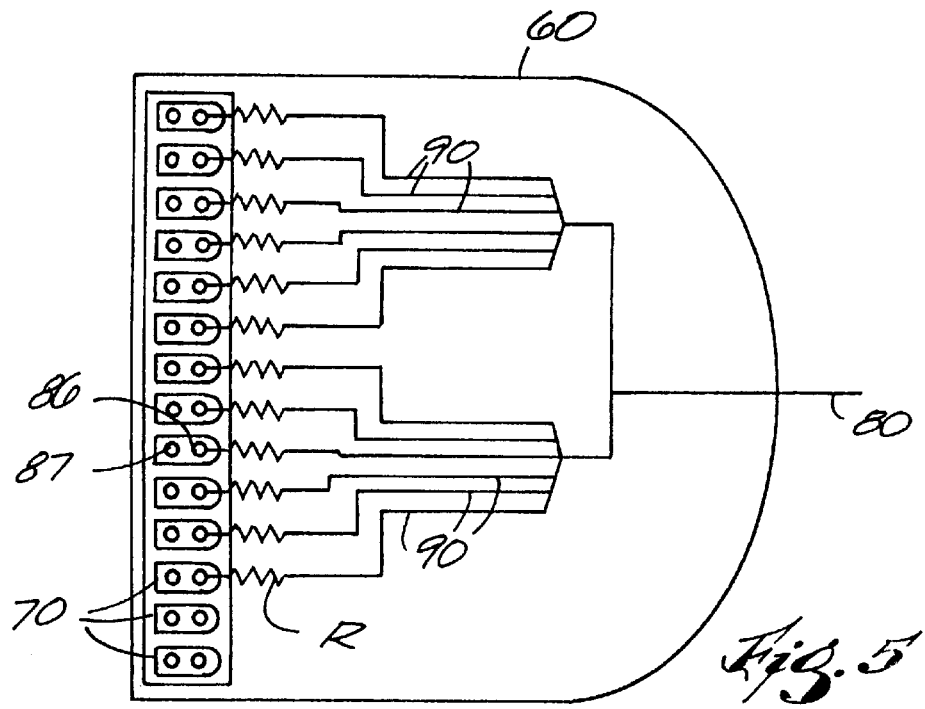
FIG. 5 schematically illustrates one embodiment of the connector block of FIG. 4.

FIG. 1 shows an intracardiac catheter 14 positioned in the heart of a patient 12. As those skilled in the art will appreciate, the catheter 14 typically comprises an elongate plastic member having one or more electrodes and/or sensors at its distal end which is positioned in a body cavity. In the illustrated example, the catheter 14, comprises an intracardiac catheter positioned in the patient's heart. Such conventional intracardiac catheters commonly include a bare metal pin connector for connection to a patient monitor. The invention comprises a connector assembly which includes an adapter 16, connects a terminal block 18 and cable 20 for connecting the catheter 14 to a patient monitor and/or strip chart recorder 22. It will be appreciated that the intracardiac catheter 14 may include a plurality of electrodes and/or sensors, each of which is connected to the terminal block 18 by an individual adapter 16 as shown in FIG. 1.

An adapter 16 is shown in greater detail in FIGS. 2 and 3 to include an insulated conductor 24 having a first connector 26 at one end for connection to the catheter 14 and a second connector 28 at its opposite end for connection to the terminal block 18. The first terminal 26 includes an elongate, insulating cover 30 which receives the pin connector 32 on the end of the catheter 14. Disposed within the cover 30 are a plurality of flexible conductive terminals 34 which are connected to the conductor 24 and surround and resiliently engage the pin connector 32. At the junction between the cover 30 and the conductor 24, there is a stress relief body 36. The conductor 24 includes a conductive wire 38 covered by a layer 40 of a flexible, suitable insulating material.

The second connector 28 includes a terminal block 42 having a head portion 44 for supporting second and fourth terminals 46 and 47 formed of a conductive material and fixedly extending from the head portion 44 in a parallel spaced apart relation. The upper ends 48 of the second and fourth terminals 46 and 47 have a reduced diameter and extend through spaced apart openings 49 in the head portion 44 and are electrically separated from each other by a partition 50 extending upwardly from the head portion 44. A skirt 51, formed of a suitable insulating material, extends from the head portion 44 in surrounding relation to the second and fourth terminals 46 and 47. A second partition 52 is disposed in the skirt 51 and between the second and fourth terminals 46 and 47 for providing electrical isolation.

The head portion 44 is received in a shell assembly formed of a suitable insulating material and consisting of an inner shell 53 and an outer shell 54. The inner shell 53 is hollow and its lower end is open for being suitably affixed over the head portion 44. There is also an opening 56 in the rear of the inner shell 53 for receiving the conductor 24. The outer shell 54 is also hollow and open at its lower end for being received over the inner shell 53 to which it is suitably attached. A hollow cone 58 extends from the rear of the outer shell portion 54 and communicates with the hollow interior thereof for receiving the conductor 24. The bare wire 38 of conductor 24 is connected to the upper end 48 of one of the second and fourth terminals 46 and 47.

The terminal block 18 shown in FIG. 4 to include a hollow housing 60 open at its upper end and including a bottom wall 61 and a side wall 62. A mounting plate 63 is supported in the housing 60 by a plurality of support posts 64 extending upwardly from the bottom wall 61 and is resiliently held in position by a pair of flat spring members 65 which are mounted on the opposite sides of side wall 62 and engage notches 66 in plate 63.

At the forward end of the support plate 63 there is a row of sockets 70 for coupling to the second connectors 28 of the adapter 16. The terminal block 18 also a cover plate 72 which is secured to the open upper end of the housing 60 and has a window 75 formed at one end for permitting access to the row of sockets 70. The housing 60 also has a rear opening 75 for receiving one end of the cable 20. In particular, the cable 20 has a conical stress relief member 76 adjacent one end and which includes a generally rectangular groove 78 complementary to the periphery of the opening 75. When the groove 78 is disposed in the opening 75, a bundle of individual conductors 80 extend into the housing 60 for connection to the sockets 70 as will be discussed below. At the opposite end of the cable 20 is a connector 82 for coupling to the monitor 22.

As shown in FIG. 3, each socket 70 has an inner surface 84 complementary to the outer surface of the skirt 51 of the connector 28. In addition, each socket 70 has a par of parallel, spaced apart, third and fifth terminals 86 and 87 which are snugly received within the sockets 46 and 47, respectively, of the second connector 28.

Figure 6:
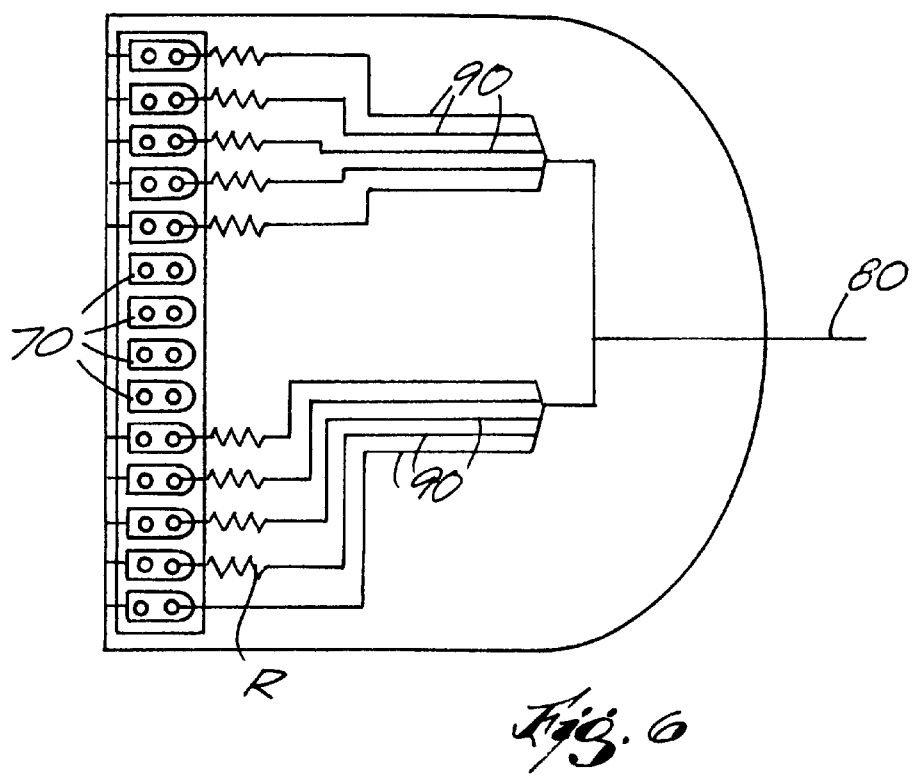
FIG. 6 schematically illustrates an alternate embodiment of the connector block shown in FIG. 4, and FIG. 7 schematically illustrates an alternate embodiment of the connector block shown in FIG. 4.
Figure 7:
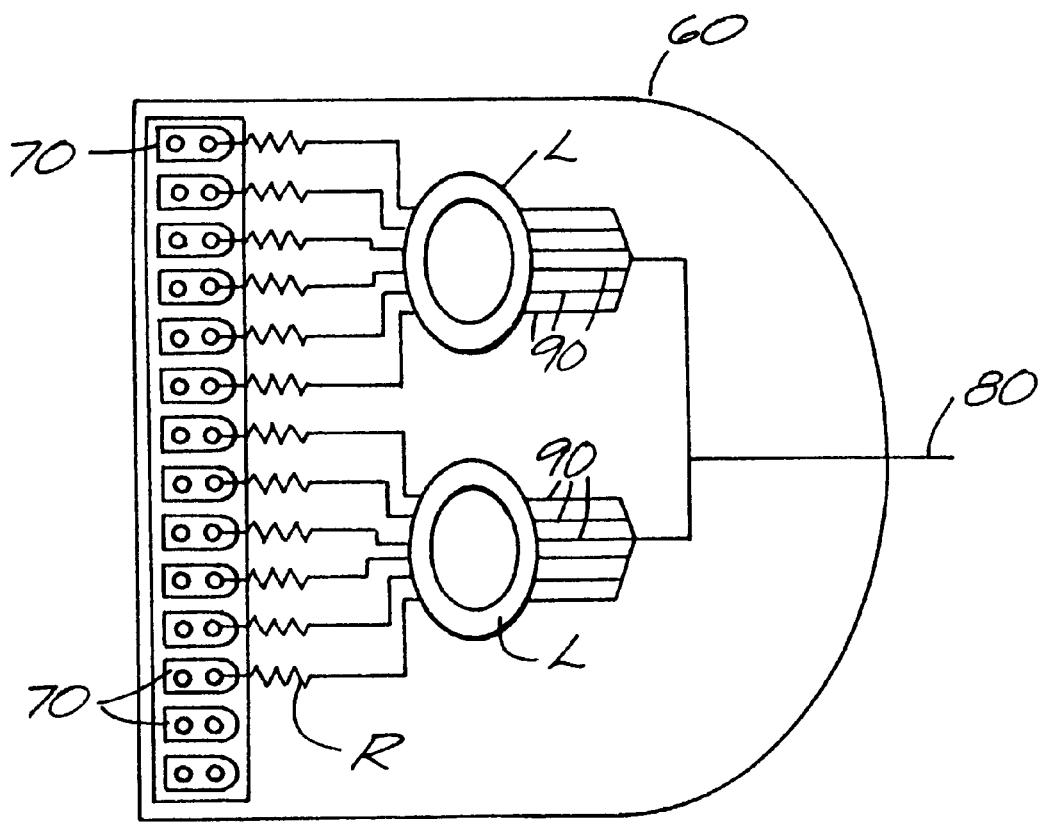

FIG. 5 schematically illustrates one embodiment of the terminal block according to the invention. In the illustrated embodiment, the wire bundle 80 includes twelve conductors 90, each of which is connected to a different one of the third terminals 86 of each socket 70. Resistors R may be interposed between each lead wire 90 and the third terminals 86. If all of the sockets 70 are not required, some may be blocked off as shown in FIG. 6. It should be appreciated that those sockets 70 which are not connected to the intracardiac leads may be connected to other electrodes, such as surface electrodes or other sensors. In addition to the resistor R, choke coils L may also be imposed in the conductors 90 if filtering is required as shown in FIG. 7.

While only a single embodiment of the invention is illustrated and described, it is not intended to be limited thereby but only by the scope of the appended claims.

I claim:

1. A connector assembly for use in connecting an intracardiac catheter having a bare end connector to a patient monitor, said assembly including an adapter having an elongate insulating conductive member defined by an intermediate portion and opposite ends, a first connector mounted at one end of the conductive member and electrically connected thereto and a second connector at the other end of the conductive member, said first connector including a first terminal connected to the conductive member for electrically engaging a bare pin connector in a surrounding relation and a tubular insulating cover extending from the one end of the adapter for telescopingly receiving the first terminal and the bare pin connector, said second connector including a second terminal connected to the conductive member and extending from the other end of the conductive member, an insulating skirt mounted on the second connector in surrounding relation to the second terminal, a terminal block having a plurality of sockets, each socket comprising a recess complementary to the insulating skirt for receiving and securing the skirt therein, and a plurality of third terminals one of which is disposed in each socket and each being electrically engageable with the second terminal, and a cable having a plurality of individual conductors each connected at one end respectively to one of said third terminals, said cable having a plug at its other end for connection to a patient monitor.

2. The assembly set forth in claim 1 wherein said second connector includes a fourth terminal disposed within said skirt and extending in a generally parallel, spaced relation to said second terminal, and a fifth terminal disposed within said socket and extending in a spaced apart parallel relation to the third terminal, said third and fifth terminals being complementary to and engageable by said second and fourth terminals.

3. The assembly set forth in claim 1 and including impedance means disposed in said terminal block and electrically connected between said individual conductors and the respective third terminals.

4. The assembly set forth in claim 1 wherein said second connector and said insulating skirt extend generally perpendicularly from said other end of the conductive member.

5. The assembly set forth in claim 4 wherein said second connector includes a fourth terminal disposed within said skirt and extending in a generally parallel, spaced relation to said second terminal, and a fifth terminal disposed within said socket and extending in a spaced apart parallel relation to the third terminal, said third and fifth terminals being complementary to and engageable by said second and fourth terminals.

6. The assembly set forth in claim 5 and including impedance means disposed in said terminal block and electrically connected between said individual conductors and the respective third terminals.

* * * * *